(12) United States Patent
Okada et al.

(10) Patent No.: US 12,606,845 B2
(45) Date of Patent: Apr. 21, 2026

(54) METHOD FOR PRODUCING NUCLEIC ACID-ENCAPSULATED AAV HOLLOW PARTICLE

(71) Applicants: NIPPON MEDICAL SCHOOL FOUNDATION, Tokyo (JP); TAKARA BIO INC., Shiga (JP)

(72) Inventors: Takashi Okada, Tokyo (JP); Junichi Mineno, Kusatsu (JP); Hideto Chono, Kusatsu (JP)

(73) Assignees: NIPPON MEDICAL SCHOOL FOUNDATION, Tokyo (JP); TAKARA BIO INC., Shiga (JP)

( * ) Notice: Subject to any disclaimer, the term of this patent is extended or adjusted under 35 U.S.C. 154(b) by 1102 days.

(21) Appl. No.: 17/622,022

(22) PCT Filed: Jul. 2, 2020

(86) PCT No.: PCT/JP2020/025961
§ 371 (c)(1),
(2) Date: Dec. 22, 2021

(87) PCT Pub. No.: WO2021/002412
PCT Pub. Date: Jan. 7, 2021

(65) Prior Publication Data
US 2022/0235375 A1 Jul. 28, 2022

(30) Foreign Application Priority Data
Jul. 3, 2019 (JP) ................................. 2019-124647

(51) Int. Cl.
*C12N 15/86* (2006.01)
*C12N 7/00* (2006.01)

(52) U.S. Cl.
CPC .............. *C12N 15/86* (2013.01); *C12N 7/00* (2013.01); *C12N 2750/14142* (2013.01); *C12N 2750/14152* (2013.01)

(58) Field of Classification Search
CPC .................... C12N 15/86; C12N 7/00; C12N 2750/14142; C12N 2750/14152
See application file for complete search history.

(56) References Cited

U.S. PATENT DOCUMENTS

| | | | |
|---|---|---|---|
| 5,863,541 A | 1/1999 | Samulski et al. | |
| 9,610,354 B2 | 4/2017 | Okada et al. | |
| 11,191,733 B2 | 12/2021 | Okada et al. | |

| | | | |
|---|---|---|---|
| 2014/0044794 A1 | 2/2014 | Okada et al. | |
| 2017/0172936 A1 | 6/2017 | Okada et al. | |
| 2022/0047521 A1 | 2/2022 | Okada et al. | |

FOREIGN PATENT DOCUMENTS

| | | |
|---|---|---|
| WO | 2012/144446 | 10/2012 |
| WO | 2013/033407 | 3/2013 |
| WO | 2018/139637 | 8/2018 |

OTHER PUBLICATIONS

Yan Z, et al. J Virol. Jan. 2005;79(1):364-79 (Year: 2005).*
Nahreini, P, et al. Gene 119.2 (1992): 265-272 (Year: 1992).*
Chiorini JA, et al. J Virol. Nov. 1994;68(11):7448-57 (Year: 1994).*
Nash, Kevin, et al. Journal of virology 82.3 (2008): 1458-1464 (Year: 2008).*
Office Action issued Dec. 11, 2023 in corresponding Chinese Patent Application No. 202080061553.1, with English translation, 21 pages.
Zhou et al., "Deletion of the B-B' and C-C' regions of inverted terminal repeats reduces rAAV productivity but increases transgene expression", Scientific Reports, 2017, vol. 7, No. 1:5432, pp. 1-13.
Musatov et al., "A cis-Acting Element That Directs Circular Adeno-Associated Virus Replication and Packaging", Journal of Virology, Dec. 2002, vol. 76, No. 24, pp. 12792-12802.
International Preliminary Report on Patentability and Written Opinion of the International Searching Authority issued Jan. 13, 2022 in the International (PCT) Application No. PCT/JP2020/025961.
International Search Report issued Sep. 8, 2020 in International (PCT) Application No. PCT/JP2020/025961.
Extended European search report issued Jul. 7, 2023 in European Patent Application No. 20835079.3.
Office Action issued Apr. 23, 2024 in corresponding Japanese Patent Application No. 2021-529175 with English machine translation.
Office Action issued Sep. 22, 2025 in corresponding Korean Patent Application No. 10-2022-7000621, with English machine translation.

* cited by examiner

*Primary Examiner* — Marcia S Noble
*Assistant Examiner* — Zanna Maria Beharry
(74) *Attorney, Agent, or Firm* — Wenderoth, Lind & Ponack, L.L.P.

(57) ABSTRACT

A method for producing a nucleic acid-encapsulated adeno-associated virus (AAV) hollow particle, comprising the following steps: (1) preparing a linear nucleic acid fragment comprising a sequence for A region and a sequence for D' region in an AAV inverted terminal repeat (ITR) (i.e., an AD sequence) or a sequence complementary to the AD sequence and a target gene sequence; (2) introducing the nucleic acid fragment prepared in step (1) into a cell capable of producing an AAV hollow particle; and (3) culturing the cell obtained in step (2).

17 Claims, 6 Drawing Sheets

Specification includes a Sequence Listing.

Plasmid AD(-)    Plasmid AD(+)    PCR product AD(-)    PCR product AD(+)

Plasmid (weight ratio)    PCR product (weight ratio)    Plasmid (molar ratio)    PCR product (molar ratio)

METHOD FOR PRODUCING NUCLEIC ACID-ENCAPSULATED AAV HOLLOW PARTICLE

TECHNICAL FIELD

The present invention relates to a method for producing empty AAV particles encapsulating a nucleic acid.

BACKGROUND ART

Various gene introduction techniques have been developed for introducing and expressing a gene of interest in mammalian cells, tissues or individuals including humans. One of the techniques is a viral vector. Various vectors derived from lentivirus, oncoretrovirus, adenovirus, adeno-associated virus and the like are known.

Among them, the adeno-associated virus (AAV) vector has been recently expected as a useful vector for gene introduction in gene therapy. AAV is a non-pathogenic virus belonging to Parvoviridae. Since AAV lacks self-renewal ability, AAV cannot grow autonomously and requires co-infection with adenovirus or herpesvirus for its growth. Thus AAV has low transmission capability. AAV also has low immunogenicity in a host. Due to such characteristics, AAV has the advantage of being highly safe as a vector for gene introduction. In addition, AAV has a broad host range and therefore various cells can be infected with AAV. Since vectors derived from various serotypes of AAV (for example, AAV1 to AAV9) have been developed, the vectors have been used for gene introduction into specific cells, tissues and organs such as nerve cells, muscle cells and hepatocytes by utilizing the specificity for target cells to be infected with each serotype. However, the conventional viral vectors including AAV have various problems including problems about acquisition of self-renewal ability and contamination with wild-type virus.

In order to solve the problems as described above, Samulski et al. suggested preparing a capsid constituting outer shell protein of AAV and using the capsid as a delivery carrier of a drug (Patent Literature 1). Though empty AAV particles that are formed by capsids and do not contain AAV virus genome inside have the virus' initial infectious activity including specific recognition of target cells, adsorption to and invasion into the cells and uncoating, the empty AAV particles do not have the viral growth activity because they do not have virus-derived genes necessary for self-renewal. Therefore, the empty particles can specifically deliver drugs such as protein or nucleic acid to target cells, and are carriers for an ideal drug delivery system (DDS: Drug Delivery System) having safety for administered individuals.

Samulski et al. suggested an introduction method comprising denaturing the empty particles in the presence of urea or under a condition of heat or pH, incorporating a drug into the inside of the denatured empty particles, and then reconstituting the empty particles (Patent Literature 1). However, when the empty particles are treated with a denaturing agent such as urea, the initial infectious activity that the capsid has is lowered and the function as a delivery carrier is impaired. In addition, Okada et al. disclosed a method for introducing a protein or a nucleic acid into empty particles comprising use of a surfactant (Patent Literature 2).

It is known that in the process of AAV replication, the DNA genome may take the form of a circular double-stranded DNA (CAAV). This double stranded DNA has one inverted terminal repeat (ITR) sequence. Musatov et al. have reported that the replication and encapsulation of AAV genomic DNA require a sequence (AD sequence) consisting of a sequence of region A and a sequence of region D' in the ITR (Non-Patent Literature 1). Musatov et al. have disclosed that the circular double stranded DNA containing the AD sequence is introduced into a cells to produce empty AAV particles encapsulating the DNA. In addition, Okada et al. have disclosed that a nucleic acid fragment containing the AD sequence and a complementary sequence thereof (a sequence of region A' and a sequence of region D) is introduced into cells to produce empty AAV particles encapsulating a nucleic acid (Patent Literature 3).

CITATION LIST

Patent Literatures

Patent Literature 1: U.S. Pat. No. 5,863,541
Patent Literature 2: WO2012/144446
Patent Literature 3: WO2018/139637

Non-Patent Literature

Non-patent Literature 1: Musatov. et al., 2002, vol. 76, No. 24, p. 12792-12802

SUMMARY OF INVENTION

Problem to be Solved by the Invention

An object of the present invention is to develop and provide a simpler and more efficient method for encapsulating a nucleic acid in empty particles.

Solution for Problem

As a result of diligent research, the present inventors succeeded in producing empty particles in which a nucleic acid is encapsulated and which maintain viral initial infectious activity by a simpler and more efficient method. In addition, the present inventors found that the nucleic acid encapsulated in the empty particles was effectively introduced into target cells by mixing the nucleic acid-encapsulating empty particles with the target cells. The present invention is based on these findings and results, and provides the following.

That is, the present invention relates to:

[1] A method for producing an empty adeno-associated virus (AAV) particle encapsulating a nucleic acid, the method comprising:

(1) a step of preparing a linear nucleic acid fragment containing a sequence of region A and a sequence of region D' in an AAV inverted terminal repeat sequence (ITR) (an AD sequence) and/or a complementary sequence of the AD sequence, and a sequence of a gene of interest, (2) a step of introducing the nucleic acid fragment prepared in step (1) into a cell that produces an empty AAV particle, and (3) a step of culturing the cell obtained in step (2);

[2] The method according to [1], wherein the nucleic acid fragment contains the AD sequence and/or the complementary sequence of the AD sequence, and the sequence of the gene of interest in order from the 5' end to the 3' end;

[3] The method according to [1], wherein the nucleic acid fragment contains the sequence of the gene of interest, and the AD sequence and/or the complementary sequence of the AD sequence in order from the 5' end to the 3' end;

[4] The method according to [1], wherein the nucleic acid fragment does not contain a sequence of region A' in the AAV ITR;

[5] The method according to [1], wherein the step of preparing the nucleic acid fragment comprises amplification of the nucleic acid fragment by a nucleic acid amplification reaction;

[6] The method according to [1], wherein the cell that produces an empty particle is a cell into which Cap gene and Rep gene of AAV, and helper function of AAV have been introduced;

[7] The method according to [1], wherein the nucleic acid fragment is a double stranded nucleic acid or a single stranded nucleic acid;

[8] The method according to [1], wherein a region for the AD sequence in the nucleic acid fragment is a double stranded nucleic acid, and a region for the sequence of the gene of interest in the nucleic acid fragment is a single stranded nucleic acid;

[9] A linear nucleic acid fragment containing a sequence of region A and a sequence of region D' in an AAV inverted terminal repeat sequence (ITR) (an AD sequence), or a complementary sequence of the AD sequence, and a sequence of a gene of interest;

[10] The nucleic acid fragment according to [9], which contains the AD sequence or the complementary sequence of the AD sequence, and the sequence of the gene of interest in order from the 5' end to the 3' end;

[11] The nucleic acid fragment according to [9], which contains the sequence of the gene of interest, and the AD sequence or the complementary sequence of the AD sequence in order from the 5' end to the 3' end;

[12] The nucleic acid fragment according to [9], which does not contain a sequence of region A' in the AAV ITR;

[13] The nucleic acid fragment of [9], which is a double stranded nucleic acid or a single stranded nucleic acid;

[14] The nucleic acid fragment according to [9], wherein a region for the AD sequence is a double stranded nucleic acid, and a region for the sequence of the gene of interest is a single stranded nucleic acid;

[15] A nucleic acid-encapsulating empty AAV particle containing the linear nucleic acid fragment according to any one of [9] to.

Effects of the Invention

The present invention provides a method for producing an empty particle in which a nucleic acid is encapsulated more easily and efficiently. The "nucleic acid-encapsulating empty AAV particle" as used herein means an AAV-like particle in which a linear nucleic acid fragment is encapsulated and which does not carry a complete AAV genome. The nucleic acid-encapsulating empty AAV particle is different from ordinary AAV.

According to the method for producing an empty particle of the present invention, a nucleic acid of interest is encapsulated in an empty particle more easily and efficiently than the conventional method, while reduced number of virus-derived sequences results in safety and low cytotoxicity. Thus, it is possible to provide an empty particle having high safety and target cell specificity.

MODE FOR CARRYING OUT THE INVENTION

Figure 4:
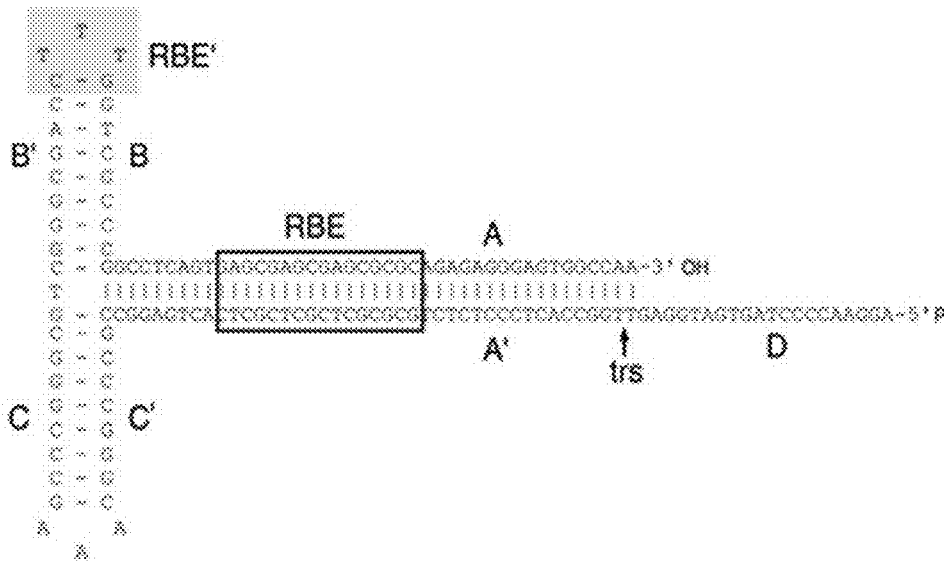
FIG. 4 shows the ITR region of AAV.
Figure 5:
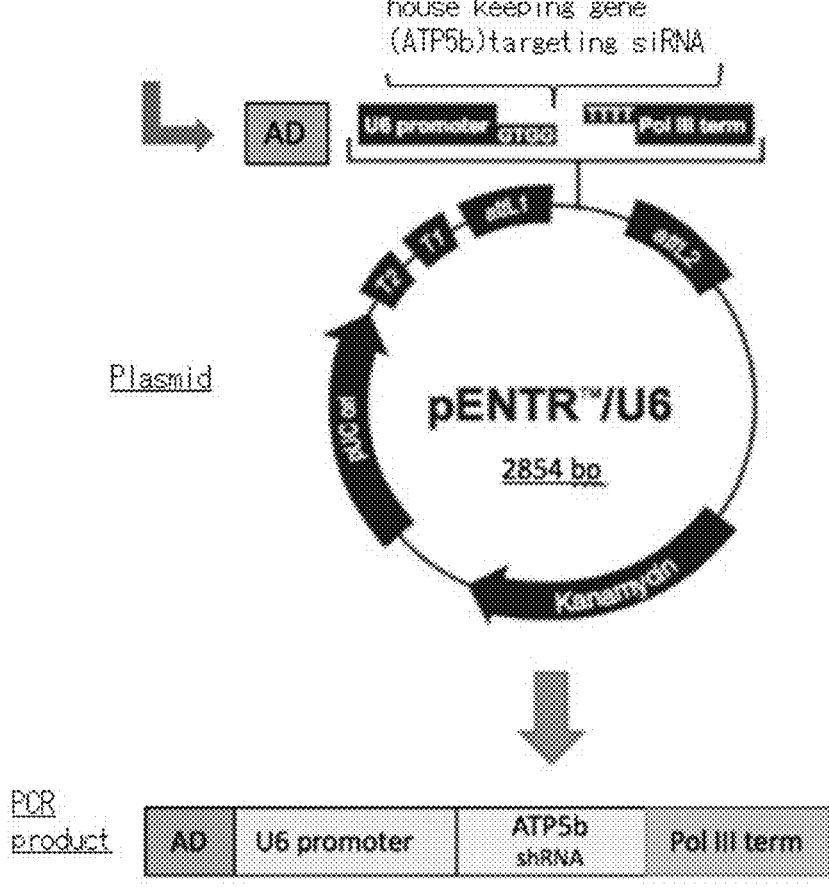
FIG. 5 shows an outline of Examples 1 to 3.

As used herein, the term "inverted terminal repeat (ITR)" means a cis element present at the both ends of AAV genomic DNA. The ITR is essential for replication, amplification and packaging of AAV genomic DNA. The ITR contains a Rep binding site (also referred to as RBS or RBE) and a terminal resolution site (TRS) as well as a palindromic sequence that allows for hairpin formation. The ITR contains region A, region B, region B', region C, region C' and region A' in this order from the end. The A region and the A' region, the B region and the B' region, and the C region and the C' region are complementary sequences to each other in the inverse direction, and anneal to form a double strand, and thus a hammer head structure as shown in FIG. 4 is formed. Region D is present at one end of the A' region which is the opposite side (3' end side or 5' end side) of the C' region.

As used herein, the term "3' end side" means a position located in the direction of 3' end beyond the 3' end portion of a sequence (region). Similarly, the term "5' end side" means a position located in the direction of 5' end beyond the 5' end portion of a sequence (region). Therefore, the term "3' end side" or "5' end side", in context, means that a sequence of interest or the like is located adjacent to the 3' or 5' end portion of a sequence (region), or a sequence of interest or the like is located non-adjacent to the 3' or 5' end portion of a sequence (region) [i.e., any sequence intervenes between a sequence of interest or the like and the 3' or 5' end portion of a sequence (region)].

As used herein, the "capsid" is one of elements constituting a virus particle (virion) and means a coat or shell composed of a plurality of unit proteins (capsomeres) surrounding genomic DNA or a core. As used herein, a particle composed of only capsid proteins which does not contain a viral nucleic acid, core or any other substances inside the capsid is referred to as an "empty particle", and sometimes an "empty capsid particle".

As used herein, the "gene of interest" means any gene desired to be encapsulated in empty particles and be introduced into a target cell. Examples of the gene of interest include a structural gene (e.g., a gene for a functional protein such as enzyme, transcription factor, reporter molecule, growth factor, or antigen protein, or a fragment thereof) and a regulatory gene [e.g., a gene encoding antisense DNA, functional RNA (antisense RNA, siRNA, miRNA, ribozyme, etc.) etc.]. Furthermore, the gene of interest may contain a regulatory element that controls transcription or translation, for example a promoter sequence, an enhancer sequence, a poly A addition signal sequence, a terminator sequence or the like. The gene of interest may be a sequence capable of expressing a protein or a functional nucleic acid in a cell.

Hereinafter, the present invention will be described in detail.

As one embodiment, the present invention provide a method for producing an empty AAV particle encapsulating a nucleic acid, which comprises the following steps:

(1) a step of preparing a linear nucleic acid fragment containing a sequence of region A and a sequence of region D' in an AAV inverted terminal repeat sequence (ITR) (an AD sequence), or a complementary sequence of the AD sequence, and a sequence of a gene of interest, (2) a step of introducing the nucleic acid fragment prepared in step (1) into a cell that produces an empty AAV particle, and (3) a step of culturing the cell obtained in step (2).

(A) Step of Preparing Nucleic Acid

The linear nucleic acid fragment in step (1) contains an AD sequence or a complementary sequence of the AD sequence, and a sequence of a gene of interest. As the AD sequence, a sequence of genomic DNA of a known natural AAV serotype (for example, serotype 1, 2, 3, 4, 5, 6, 7, 8, 9, 10 or 11) can be used. In the ITR of each serotype, region A, region B, region B', region C, region C', and region A' have been identified. Region D is present at one end of the A' region in the ITR which is the opposite side (3' end side or 5' end side) of the C' region. A sequence of region D of each serotype and a sequence of region D' that is a complementary sequence to the sequence of region D in the inverse direction have also been identified. The A region, the A' region, the D region and the D' region may be derived from different serotypes. Furthermore, a mutant of the natural sequence of the A region can be also used as long as it retains the ability to bind to Rep and the ability to form a hairpin. In such a case, the sequence of the A' region is complementary to the mutant sequence of the A region. In addition, a mutant of the natural sequence of the D region can be also used, and in such a case, the sequence of the D' region is complementary to the mutant sequence of the D region.

The linear nucleic acid fragment used in the present invention does not contain the sequence of the A' region (SEQ ID NO: 8). In other words, the sequence of the A region contained in the linear nucleic acid fragment does not anneal intramolecularly, and thus the sequence of the A region does not form a secondary structure. Furthermore, the linear nucleic acid fragment does not contain a sequence consisting of the D region sequence-the A' region sequence in a direction from the 5' end to the 3' end. In other words, the AD sequence contained in the linear nucleic acid fragment does not anneal intramolecularly, and thus the AD sequence does not form a secondary structure. Further, the nucleic acid fragment lacks a sequence of at least one region selected from the group consisting of region B, region B', region C and region C'. More preferably, the nucleic acid fragment lacks sequences of region B, region B', region C and region C'.

In an aspect of the present invention, the linear nucleic acid fragment in step (1) contains an AD sequence or a complementary sequence of the AD sequence, and a sequence of a gene of interest in a direction from the 5' end to the 3' end. In an additional aspect, the linear nucleic acid fragment contains a sequence of a gene of interest, and an AD sequence or a complementary sequence of the AD sequence in a direction from the 5' end to the 3' end.

The linear nucleic acid fragment in step (1) contains a sequence of a gene of interest. The gene of interest may be foreign to AAV.

The linear nucleic acid fragment in step (1) contains at least one AD sequence or a complementary sequence of the AD sequence. In the present invention, the nucleic acid fragment may contain one AD sequence or one complementary sequence of the AD sequence, two AD sequences or complementary sequences of the AD sequence, three AD sequences or complementary sequences of the AD sequence, four AD sequences or complementary sequences of the AD sequence, or five or more AD sequences or complementary sequences of the AD sequence. For example, the nucleic acid fragment containing one, two or three AD sequences or complementary sequences of the AD sequence can be used.

The linear nucleic acid fragment in step (1) is DNA or RNA, preferably DNA. Further, the nucleic acid fragment may be a double stranded nucleic acid formed by annealing of two nucleic acid molecules complementary to each other, or may be a single stranded nucleic acid of one molecule. The term "linear nucleic acid" means that both ends of a nucleic acid are not bound by a covalent bond. Further, the entire sequence of the nucleic acid fragment may be double stranded, or a part of the sequence of the nucleic acid fragment may be single stranded and the remaining part(s) of the nucleic acid may be double stranded. Foer example, in the nucleic acid fragment, the AD sequence region may be double stranded and the region of the gene sequence of interest may be single stranded. The nucleic acid fragment may be a nucleic acid fragment having no phosphate bond (nucleotide bond) at one position, two positions or a plurality of positions in the double stranded portion. As an aspect of the present invention, the linear nucleic acid fragment is a double stranded nucleic acid obtained by annealing three molecules of a single stranded nucleic acid containing a sequence of a gene of interest, a single stranded nucleic acid containing an AD sequence, and a single stranded nucleic acid complementary to the sequence of the gene of interest and the AD sequence. It is natural that a double stranded nucleic acid containing an AD sequence contains a complementary strand to the AD sequence, and a double stranded nucleic acid containing a complementary strand to an AD sequence contains the AD sequence.

The linear nucleic acid fragment in step (1) can be prepared by a known nucleic acid preparation method. The nucleic acid fragment can be prepared in vitro by nucleic acid amplification reaction such as PCR or chemical synthesis. In addition, the nucleic acid can be prepared by producing a nucleic acid in vivo such as in eukaryotic cells and prokaryotic cells by polymerase reaction, replication and/or transcription and then purifying the nucleic acid from the cells. The linear nucleic acid fragment itself is also included in the present invention as an aspect.

As an aspect of the present invention, the AD sequence contained in the linear nucleic acid fragment in step (1) is a sequence derived from AAV2, and the sequence of the A region and the sequence of the D' region are shown in SEQ ID NO: 9 and SEQ ID NO: 10, respectively. Further, the sequences of the A' region and the D region from AAV2 are shown in SEQ ID NO: 8 and SEQ ID NO: 11, respectively. Further, the AD sequence from AAV2 is shown in SEQ ID NO: 1, and the complementary sequence to the AD sequence is shown in SEQ ID NO: 18.

Examples of the nucleic acid fragment in step (1) include a natural nucleic acid, a chemically modified nucleic acid, an artificial nucleic acid, a nucleic acid analog, and a combination thereof. The natural nucleic acid is DNA or RNA consisting of only naturally occurring nucleotides being linked to one another. The chemically modified nucleic acid is an artificially chemically modified nucleic acid. Examples of the chemically modified nucleic acid include methylphosphonate DNA/RNA, phosphorothioate DNA/RNA (PS-DNA/RNA), phosphoramidate DNA/RNA, and 2'-O-methyl DNA/RNA. The artificial nucleic acid is a nucleic acid partially comprising a non-natural nucleotide(s) in a naturally occurring nucleic acid, or a nucleic acid consisting of only non-natural nucleotides being linked to one another. The term "non-natural nucleotide" as used herein refers to an artificially constructed or artificially chemically modified nucleotide that does not exist in nature and has property and/or structure similar to that of the naturally occurring nucleotide. The nucleic acid analog is an artificially constructed high molecular compound having structure and/or property similar to that of a naturally occurring nucleic acid. Examples of the nucleic acid analog include a peptide nucleic acid (PNA), a peptide nucleic acid having a phosphate group (PHONA), 2'-F, 2'-O-methyl (2'-OMe), 2'-O-methoxyethyl (2'-MOE), a bridged nucleic acid, and a morpholino nucleic acid (including morpholino oligo). Examples of the bridged nucleic acid include a bridged nucleic acid and/or a locked nucleic acid (BNA/LNA), and ENA (2'-O, 4'-C-Ethylene-BNA). As an aspect of the present invention, in the nucleic acid fragment, the region of the AD sequence or a complementary sequence of the AD sequence is a naturally occurring nucleic acid, and the region of a gene sequence of interest is an artificial nucleic acid.

In the nucleic acid, its phosphate group, sugar and/or base may be labeled if necessary. As the label, a labeling substance known in the art can be used. Examples of the labeling substance include radioisotopes (for example, 32P, 3H, 14C), DIG, biotin, fluorescent dyes (for example, FITC, Texas, cy3, cy5, cy7, FAM, HEX, VIC, JOE, Rox, TET, Bodypy 493, NBD, TAMRA), and luminescent substances (for example, acridinium ester).

As the nucleic acid fragment in step (1), a nucleic acid purified/extracted by using a known purification method or a commercially available product can be used. Examples of a known purification method include extraction with a phenol/chloroform mixture, alcohol precipitation, column purification, filtration using a filter, and agarose gel electrophoresis.

The size of the nucleic acid fragment is not limited as long as it can be encapsulated in an empty AAV particle, and is usually 5 kb or less. The nucleic acid fragment in step (1) does not contain the natural full sequence of an AAV genome, and lacks the sequence of the Rep gene of AAV and/or the sequence of the Cap gene of AAV. The nucleic acid fragment does not retain the natural full ITR sequence.

(B) Step of Introducing Nucleic Acid into Cell

The nucleic acid fragment in step (1) is introduced into a cell that produces empty particles of AAV. Examples of the cell into which the nucleic acid fragment is introduced include various eukaryotic cells such as, mammalian cells including mouse cells and primate cells (for example, human cell), and insect cells. As used herein, the cell that produces AAV or empty particles in which a nucleic acid will be encapsulated may also be referred to as a packaging cell or a producer cell. Suitable examples of the mammalian cells include, but are not limited to, primary cells and cell lines. Suitable examples of the cell lines include HEK293 cell, 293EB cell, COS cell, HeLa cell, Vero cell, 3T3 mouse fibroblast, C3H10T1/2 fibroblast, CHO cell and cells derived from these cells. Suitable examples of the insect cells include, but are not limited to, primary cells and cell lines. Suitable examples of the cell lines include Sf9 cell and its derived cell lines.

As the cell that produces empty particles, a cell expressing the AAV rep gene product and the cap gene product is used. These gene products may be encoded by the AAV rep gene and cap gene stably integrated into the cell genome, and may be encoded by a vector that is introduced into the cell before, simultaneously with, or after the introduction of the nucleic acid fragment. When the rep gene and the cap gene are encoded by the vector, the rep gene and the cap gene may be encoded by a single vector or by separate vectors. The rep gene and the cap gene may be sequences of any AAV serotype (e.g., serotype 1, 2, 3, 4, 5, 6, 7, 8, 9, 10 or 11). Furthermore, the rep gene and the cap gene may be sequences derived from the same serotype or may be sequences derived from different serotypes.

The vector encoding the rep gene and the cap gene may be an expression vector suitable for a cell into which the vector is introduced as long as the cell can produce empty particles. Examples of the vector include viral vectors, plasmid vectors, cosmid vectors, and artificial chromosomes. The plasmid vector may be, if necessary, a vector that can be maintained episomally. The vector may be placed under the control of a promoter and a terminator within a suitable expression system so that the rep and cap genes can be expressed intracellularly. The expression system for nucleic acid is a system comprising at least one set of expression regulatory elements required for gene expression in a functional state. Examples of the expression regulatory element include a promoter and a terminator, and if necessary, an enhancer and a poly(A) signal.

A helper function may be further introduced into the cell that produces empty particles. The helper function is also called a helper virus function or an accessory function. For introduction of the helper function, though adenovirus is generally used, viruses such as herpes simplex virus type 1 or type 2 and vaccinia virus can also be used. When using a virus, the cell is infected with the virus as a helper virus. For example, because only expression of early genes of adenovirus is required for packaging of AAV particles, an adenovirus that does not express late genes may be used. An adenovirus mutant lacking late gene expression (e.g., ts100K or ts149 adenovirus mutant) can be used. Alternatively, nucleic acids required for the helper virus function which is isolated from the helper virus can be used to prepare a nucleic acid construct that provides the helper virus function, and the nucleic acid construct can be introduced into the cell. The construct that provides the helper virus function contains a nucleotide sequence for providing one or more helper virus functions including an E1 gene region, an E2A gene region, an E4orf6 gene, and a gene encoding a VA RNA, and is provided as the form of a plasmid, a phage, a transposon, a cosmid or another virus to the host cell.

For introducing the nucleic acid fragment prepared in step (1) into the cell, for example, a calcium phosphate method, a lipofection method, a DEAE dextran method, a polyethyleneimine method, an electroporation method, a direct microinjection method, a high-speed fine particle gun, or the like can be used. Commercially available reagents, for example TransIT (registered trademark)-293 Reagent (manufactured by Mirus), TransIT (registered trademark)-2020 (manufactured by Mirus), Lipofectamine™ 2000 Transfection Reagent (manufactured by Life Technologies), Lipofectamine™ 2000CD Transfection Reagent (manufactured by Life Technologies), FuGene (registered trademark) Transfection Reagent (manufactured by Promega), PEI MAX® transfection reagent (manufactured by Cosmo Bio), etc. may be also used.

The nucleic acid fragment prepared in step (1) is introduced in an amount of 1 ng to 10 μg, preferably 5 ng to 1 μg, and more preferably 10 ng to 500 ng per $10^6$ cells.

(C) Step of Culturing Cell

The cell into which the nucleic acid fragment has been introduced in above (B) can be cultured under known culture conditions depending on the type of the cell. As a non-restrictive example, the cell may be cultured under conditions of a temperature of 30 to 37° C., a humidity of 95%, and a $CO_2$ concentration of 5 to 10%. The cell culture may be carried out at a temperature, a humidity and a $CO_2$ concentration falling outside the above-mentioned ranges as long as the desired cell proliferation and production of nucleic acid-encapsulating empty particles are achieved.

As a medium for the culture, a known medium can be used. Examples of the medium include DMEM, IMDM, Ham F12, and RPMI-1640, and they are commercially available from Lonza, Thermo Fisher Scientific, Sigma-Aldrich and the like. The medium may be a serum-free medium, or may be a medium containing fetal bovine serum (FBS), human serum albumin, or the like.

As a cell culture device (vessel) for the cell culture, a petri dish, a flask, a bag, a large culture tank or a bioreactor can be used. The bag may be preferably a $CO_2$ gas permeable bag for cell culture. The large culture tank may be used if large numbers of cells are required.

A culture period is not particularly limited. For example, the cell may be cultured for 12 hours to 10 days, preferably 24 hours to 7 days. During the culture, nucleic acid-encapsulating empty particles, i.e., AAV-like particles retaining a nucleic acid inside are produced intracellularly and/or in a culture supernatant.

In the present invention, further, a step of obtaining nucleic acid-encapsulating empty particles from the cell culture supernatant or a supernatant obtained by centrifugation of a suspension (cell homogenate) of the cells collected and homogenized in a suitable buffer may be performed. In the present invention, the culture supernatant or the cell homogenate supernatant thus obtained can be directly stored by a suitable method such as freezing until before use, or can be subjected to concentration, purification, etc. of the empty particles by a known method such as filter filtration or CsCl density gradient centrifugation or by using a commercially available product, and then stored by a suitable method such as freezing until before use.

(D) Nucleic Acid-Encapsulating Empty Particle and Composition

The present invention provides an empty particle (AAV-like particle) in which the nucleic acid fragment prepared in step (1) is encapsulated. The nucleic acid-encapsulating empty particle of the present invention does not retain a natural complete AAV genome and does not retain a nucleic acid comprising the sequence of AAV Rep gene and/or the AAV Cap gene. Preferably, the nucleic acid-encapsulating empty particle of the present invention does not retain natural complete ITR sequences and does not retain region A' and region D. Further, the nucleic acid-encapsulating empty particle of the present invention does not have to retain a sequence of at least one region selected from the group consisting of region B, region B', region C and region C'. Further, the present invention provides a composition comprising the above-mentioned nucleic acid-encapsulating empty particle. The composition of the present invention is characterized by comprising at least one of the nucleic acid-encapsulating empty particles obtained by the method of the present invention.

The composition of the present invention may comprise a carrier and/or other drugs in addition to the nucleic acid-encapsulating empty particle as an active ingredient. The composition may comprise two or more different kinds of nucleic acid-encapsulating empty particles. In this case, the two or more different kinds of nucleic acid-encapsulating empty particles may comprise capsids and the like derived from different viruses and/or encapsulate different types of nucleic acids. For example, the composition may comprise two or more nucleic acid-encapsulating empty particles that target different cells. The carrier is a substance that facilitates drug preparation using the composition or application of the composition to a living body, and is added within a range that does not inhibit or suppress the effect of the composition. Examples of the carrier include, but are not limited to, an excipient, a binder, a disintegrant, a filler, an emulsifier, a flow addition modifier, and a lubricant. A pharmaceutically acceptable carrier is preferably used in the composition of the present invention.

A content of the nucleic acid-encapsulating empty particles in the composition of the present invention is not particularly limited, and is appropriately determined considering the type and/or effective amount of the nucleic acid contained in the particle, the cell or individual to which the particle is applied, the method or route of application, the purpose of application, the form (including morphology and size) of the composition, the type of the carrier, etc.

The nucleic acid-encapsulating empty particle of the present invention and the composition comprising the empty particle can be used to introduce a gene into a cell or an individual animal. Such a gene introduction method is also one aspect of the present invention. The gene introduction into a cell can be performed by contacting the composition with the cell in vitro. The gene introduction into an individual animal including human is performed by administering the composition of the present invention via a route such as intra-tissue (for example, intramuscular), intravenous, subcutaneous or intraperitoneal administration.

EXAMPLES

Hereinafter, the present invention will be more specifically explained with reference to Examples which the scope of the present invention is not limited to.

Example 1: Packaging of DNA Fragment into Empty AAV Particle by Introduction—1

(1) Preparation of DNA Fragment Containing AD Sequence

A single stranded DNA oligonucleotide set forth in SEQ ID NO: 2 which encodes shRNA targeting a human ATP5b gene, and its complementary strand were chemically synthesized as a gene of interest. They were annealed to prepare a double stranded DNA oligonucleotide. The double stranded DNA oligonucleotide was cloned into a cloning site of pENTR (trademark)/U6 vector (manufactured by Thermo Fisher Scientific) to prepare a recombinant plasmid. Further, a double stranded DNA oligonucleotide containing an AD sequence (61 bp ranging from region A to region D': SEQ ID NO: 1) present in ITR of AAV2 genomic DNA and having recognition sequences of restriction enzymes SalI and KpnI at the both ends was prepared by chemically synthesizing each strand of the double stranded DNA oligonucleotide and then annealing the two strands. This double stranded DNA fragment was inserted between the SalI site and the KpnI site upstream of the U6 promoter in the recombinant plasmid to prepare ATP5b shRNA plasmid DNA (plasmid AD+). This plasmid contains an AD sequence, a U6 promoter sequence, a shRNA sequence, and a Pol III terminator sequence in order from the 5' end to the 3' end. A control plasmid DNA (plasmid AD−) containing no AD sequence was also prepared. These plasmid DNAs were subjected to sequencing analysis and confirmed to have the intended sequences.

PCR was carried out using the plasmid DNAs as a template and M13 Forward (−20) primer and M13 Reverse primer (Thermo Fisher Scientific) to amplify the DNA fragment (PCR product AD+) and DNA fragment (PCR product AD−). A PCR reaction solution was purified using PCR Purification kit (QIAGEN), and subjected to analysis sequencing for sequence confirmation.

(2) Introduction into 293EB Cell

With the plasmid DNAs and the DNA fragments obtained in Example 1-(1) as well as pAAV2/9 (SEQ ID NO: 3) which was a plasmid expressing AAV9 Cap and AAV2 Rep and pAd5N (Agilent Technologies) which was a helper plasmid, $1 \times 10^8$ cells of 293EB cells (WO 2012/144446) were transfected using Polyethylenimine "Max" (manufactured by Cosmobio). The weight of the transfected plasmid DNA was adjusted to 44.8 µg. The weight of the DNA fragment was adjusted to 10.9 µg in terms of molar ratio. A medium for the transfection was DMEM (serum-free) containing 1/100 volume of GLUTAMAX™ cell culture supplement. After the transfection, the cells were cultured at 37° C. and 5% $CO_2$ for 5 days.

(3) Recovery of AAV-Like Particle

Figure 1:
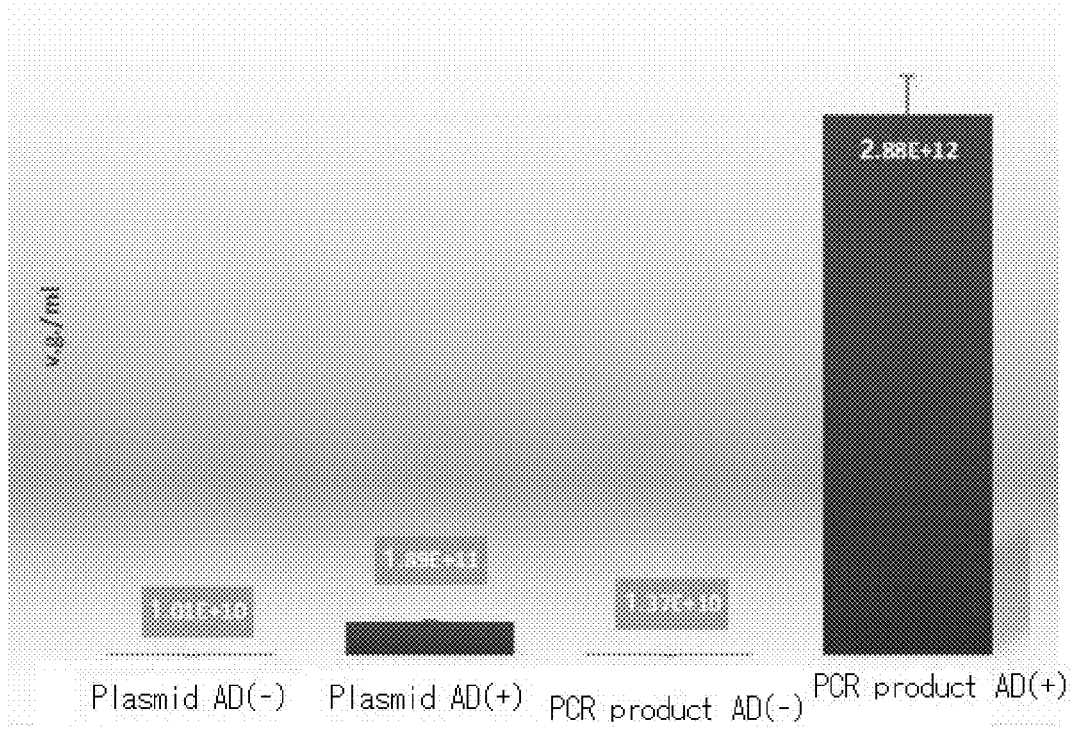
FIG. 1 shows the measured result of the titer of an empty AAV particle prepared using a linear nucleic acid fragment containing an AD sequence.

After collecting a culture supernatant of the 293EB cells cultured in Example 1-(2), DNaseI was added to the supernatant to degrade free DNA. After the degradation, AL buffer (manufactured by Qiagen) was added to the supernatant containing nucleic acid-encapsulating empty AAV particles (AAV-like particles) to dissolve the AAV capsid and extract the packaged DNA. The copy number of the plasmid DNAs and the DNA fragments contained in the AAV-like particles was analyzed by quantitative PCR using U6-F primer (SEQ ID NO: 4) and U6-R primer (SEQ ID NO: 5) (FIG. 1). As shown in FIG. 1, packaging into the empty AAV particles occurred more efficiently when transfected with the DNA fragment containing the AD sequence than when transfected with the plasmid DNA containing the AD sequence (about 15.2 times). Since such a DNA fragment can be prepared in large quantity by PCR, it is possible to prepare the AAV-like particles more easily.

Example 2: Packaging of DNA Fragment into Empty AAV Particle by Introduction—2

(1) Introduction into 293EB Cell

The plasmid DNA and the DNA fragment prepared in Example 1-(1) were introduced into 293EB cells at the same molar concentration. Specifically, 293EB cells were transfected and cultured in the same manner as in Example 1-(2) except that the DNA fragment was used in an amount of 1/4.1 (724/2974) the weight of the plasmid DNA considering the nucleotide lengths of the ATP5b shRNA plasmid DNA (2974 bp) and the DNA fragment (PCR product AD+) (724 bp).

(3) Recovery of AAV-Like Particle

Figure 2:
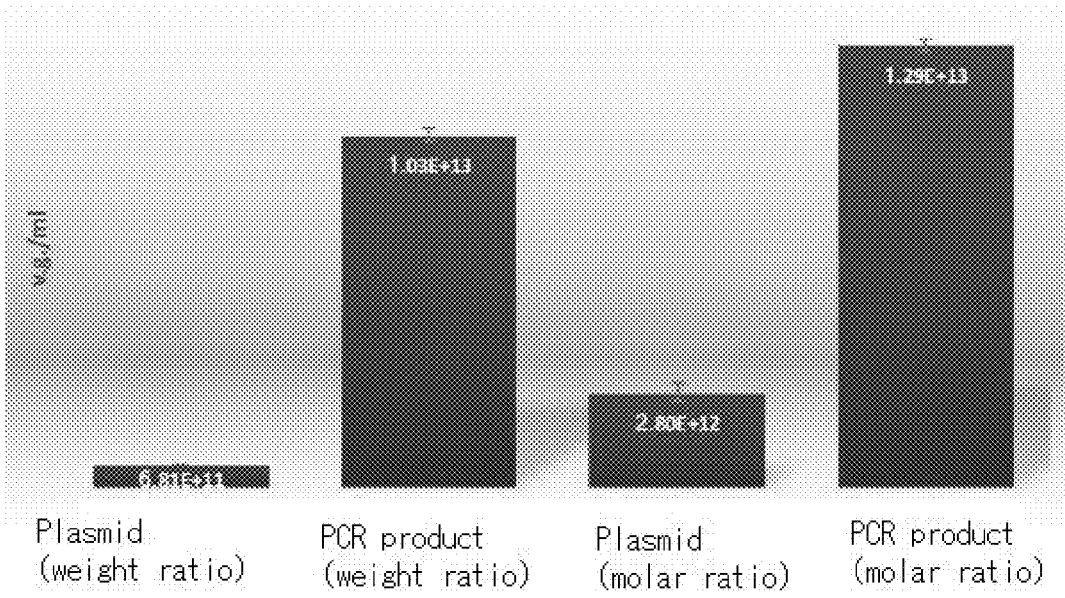
FIG. 2 shows the measured result of the titer of an empty AAV particle prepared using a linear nucleic acid fragment containing an AD sequence.

After collecting a culture supernatant of the 293EB cells cultured in Example 2-(1), Benzonase was added to the supernatant to degrade free DNA. The supernatant was heat-treated at 50° C. for 20 minutes and then centrifuged to remove precipitates. Further, AAV-like particles in the supernatant were purified by cesium chloride density gradient centrifugation. The copy number of the plasmid DNA and the DNA fragment contained in the obtained AAV-like particles was analyzed by quantitative PCR in the same manner as in Example 1-(3) (FIG. 2). As shown in FIG. 2, even in the case where the plasmid DNA and the DNA fragment were used at the same molar concentration, packaging into the empty AAV particles occurred more efficiently when transfected with the DNA fragment containing the AD sequence than when transfected with the plasmid DNA containing the AD sequence (about 4.6 times).

Example 3: Transduction of Cell by AAV-Like Particle

Figure 3:
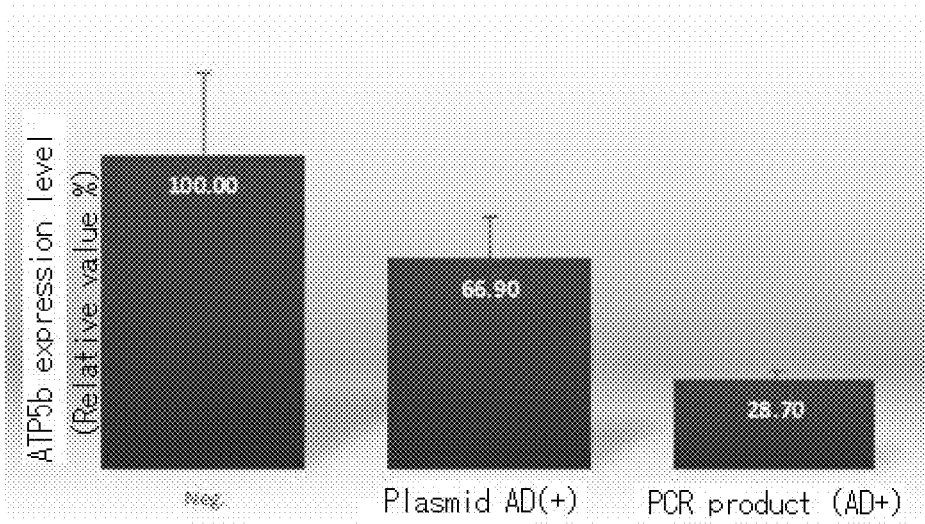
FIG. 3 shows the measured result of gene introduction by an empty AAV particle prepared using a linear nucleic acid fragment containing an AD sequence.

The AAV-like particles containing the plasmid (AD+) or the DNA fragment (PCR product AD+) prepared in Example 1-(3) were infected into HEK293 cells at $1.0 \times 10^6$ v.g./cell. Three days after the infection, RNA was extracted from the HEK293 cells using RNeasy Mini Kit (manufactured by QIAGEN). The expression level of ATP5b was analyzed by RT-PCR using primers hATP5b-F (SEQ ID NO: 6) and hATP5b-R (SEQ ID NO: 7) (FIG. 3). As shown in FIG. 3, higher knockdown of the ATP5b gene expression was observed in the cells infected with the AAV-like particles containing the DNA fragment than the cells infected with the AAV-like particles containing the plasmid DNA.

Example 4: Packaging of Modified Nucleic Acid to which AD Sequence is Added—1

(1) Preparation of Oligonucleotide

Figure 6:
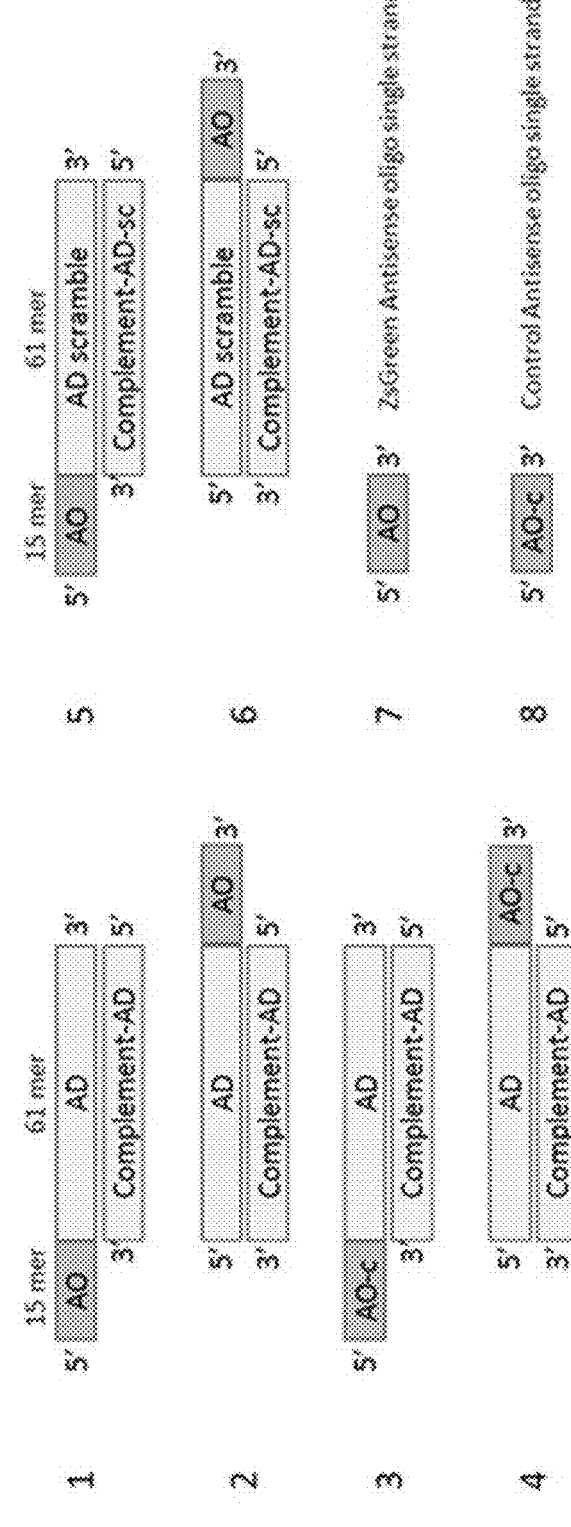
FIG. 6 shows linear nucleic acid fragments encapsulated in empty AAV particles in Example 4.

Packaging of an antisense oligonucleotide targeting a fluorescent protein ZsGreen gene sequence and containing a modified nucleic acid was performed. First, the AD sequence (SEQ ID NO: 1) was bound to the 3' end of antisense sequence AO (SEQ ID NO: 12) of the ZsGreen gene to synthesize an oligonucleotide. The linkages between nucleotides in the antisense sequence and the linkage between the antisense sequence and the AD sequence were phosphorothioate linkages (PS linkages), and the nucleotides at positions 1, 2, 3, 13 and 14 were LNA. This oligonucleotide, and a separately synthesized oligonucleotide (Complement-AD, SEQ ID NO: 18) complementary to the AD sequence and consisting of naturally occurring nucleotides were annealed to prepare a modified oligonucleotide (No. 1). Further, a modified oligonucleotide (No. 2) in which the AD sequence was bound to the 5' end of the antisense sequence was prepared. In addition, antisense oligonucleotides (No. 3 and No. 4) in which the antisense sequences in the oligonucleotides No. 1 and No. 2 were replaced with negative control sequence AO-c (SEQ ID NO: 13) were prepared, and antisense oligonucleotides (No. 5 and No. 6) in which the AD sequence in the oligonucleotides No. 1 and No. 2 was replaced with a scrambled AD sequence (SEQ ID NO: 14) were prepared. Furthermore, a single stranded oligonucleotide (No. 7) consisting of only the antisense sequence AO and a single stranded oligonucleotide (No. 8) consisting of only the negative control sequence AO-c were prepared. The structures of these oligonucleotides are shown in FIG. 6.

(2) Introduction into 293EB Cell and Recovery of AAV-Like Particle

With oligonucleotides Nos. 1-8 obtained in Example 4-(1) as well as plasmid pAAV2/9 and plasmid pAd5N, $1\times10^8$ cells of 293EB cells were transfected using Polyethylenimine "Max" in the same manner as in Example 1-(2). The transfected oligonucleotides were at concentration of 0.1, 1 and 10 nM. A medium for the transfection was DMEM (serum-free) containing $\frac{1}{100}$ volume of GLUTAMAX™ cell culture supplement. After the transfection, the cells were cultured at 37° C. and 5% $CO_2$ for 5 days.

Figure 7:
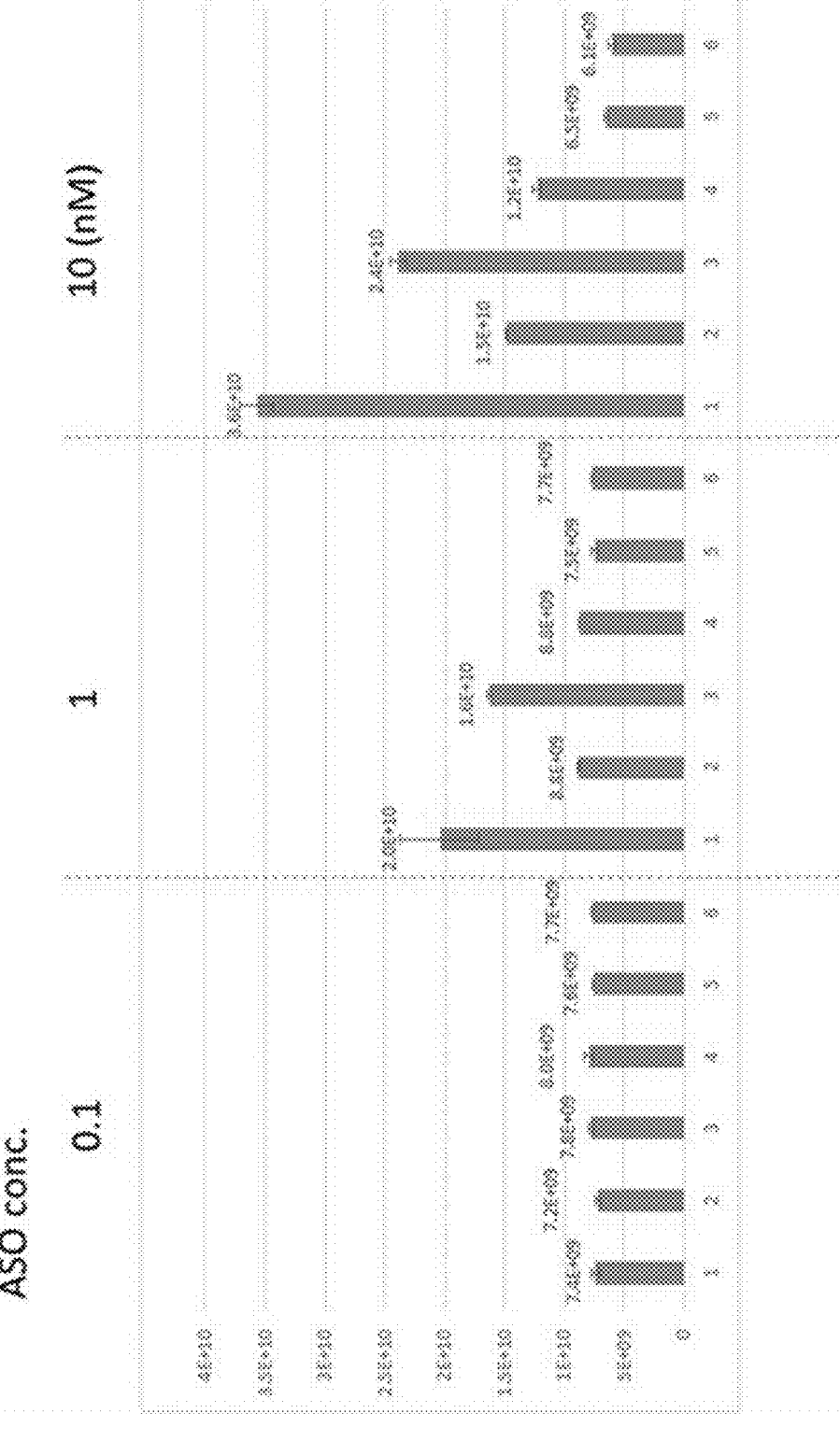
FIG. 7 shows the measured results of gene introduction by empty AAV particles prepared using linear nucleic acid fragments containing an AD sequence.

After collecting a culture supernatant of the 293EB cells, DNaseI was added to the supernatant to degrade free DNA. After the degradation, AL buffer (manufactured by Qiagen) was added to the supernatant containing nucleic acid-encapsulating empty AAV particles (AAV-like particles) to dissolve the AAV capsid and extract the packaged DNA. The copy number of the oligonucleotides contained in the AAV-like particles was analyzed by quantitative PCR using ITR-F primer (SEQ ID NO: 15) and ITR-R primer (SEQ ID NO: 16) (FIG. 7). As shown in FIG. 7, the oligonucleotides containing the AD sequence were packaged into the empty AAV particles depending on the concentration of the oligonucleotide. It was shown that the packaging occurred more efficiently when the AD sequence was bound to the 3' end of the oligonucleotide.

Example 5: Packaging of DNA Fragment into Empty AAV Particle by Introduction—3

(1) Preparation of Oligonucleotide

Figure 8:
FIG. 8 shows linear nucleic acid fragments encapsulated in empty AAV particles in Example 5.
Figure 8:
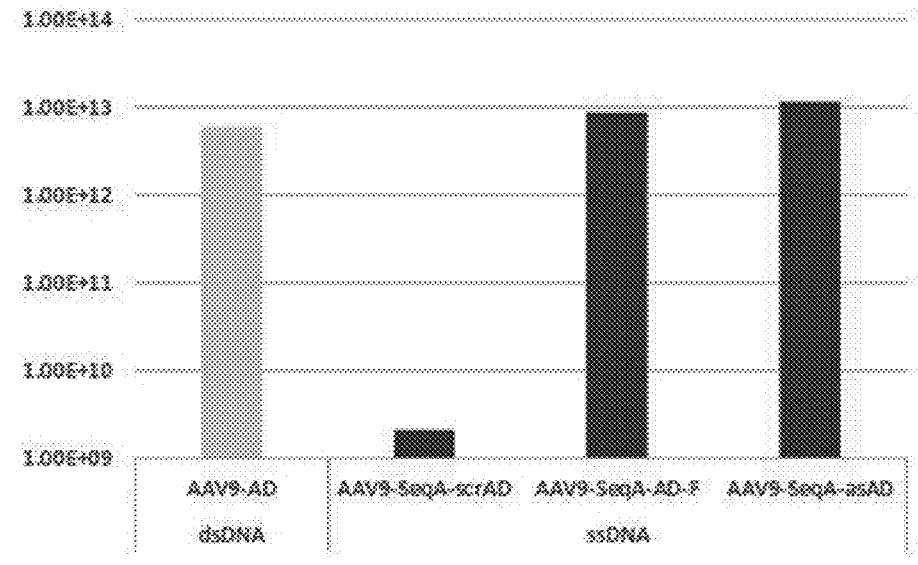

For use in exon skipping therapy for Duchenne muscular dystrophy (DMD), packaging of an antisense oligonucleotide that induces skipping of exon 23 in a dystrophin gene in DMD model mice into empty AAV particles was performed. First, the AD sequence (SEQ ID NO: 1) was bound to the 3' end of antisense sequence AO4 (SEQ ID NO: 17) of the mouse dystrophin gene to synthesize a single stranded oligonucleotide (SeqA-AD-F). In addition, a complementary sequence to the AD sequence (Complement-AD, SEQ ID NO: 18) was bound to the 3' end of the antisense sequence AO4 (SEQ ID NO: 17) to synthesize a single stranded oligonucleotide (SeqA-asAD). The scrambled AD sequence (SEQ ID NO: 14) was bound to the 3' end of the antisense sequence AO4 (SEQ ID NO: 17) to synthesize a single stranded oligonucleotide (SeqA-scrAD). Furthermore, the separately synthesized oligonucleotide complementary to the AD sequence (Complement-AD, SEQ ID NO: 18) and the oligonucleotide SeqA-AD-F were annealed to prepare an oligonucleotide (AD) in which the AD sequence region was double stranded and the antisense sequence region was single stranded. The structures of these oligonucleotides is shown in FIG. 8.

(2) Introduction into 293EB Cell and Recovery of AAV-Like Particle

With the oligonucleotides obtained in Example 5-(1) as well as plasmid pAAV2/9 and plasmid pAd5N, $1.25\times10^8$ cells of 293EB cells were transfected using Polyethylenimine "Max" in the same manner as in Example 1-(2). The transfected oligonucleotides were at concentration of 30 nM. A medium for the transfection was DMEM (serum-free) containing $\frac{1}{100}$ volume of GLUTAMAX™ cell culture supplement. After the transfection, the cells were cultured at 37° C. and 5% $CO_2$ for 5 days.

After collecting a culture supernatant of the 293EB cells, AAV-like particles were purified using AAVpro (registered trademark) Concentrator (manufactured by Takara Bio Inc.). The copy number of the oligonucleotides contained in the AAV-like particles was analyzed by quantitative PCR using ITR-F primer (SEQ ID NO: 15) and ITR-R primer (SEQ ID NO: 16) (FIG. 8). As shown in FIG. 8, the single stranded oligonucleotides containing the AD sequence and/or the complementary sequence to the AD sequence were packaged into the empty AAV particles.

INDUSTRIAL APPLICABILITY

According to the present invention, a simpler and more efficient method for encapsulating nucleic acid in empty particles is provided. The nucleic acid-encapsulating empty particles produced by the method of the present invention and a composition comprising the nucleic acid-encapsulating empty particle as an active ingredient are useful as a gene introduction means in the research or clinical practice fields of gene therapy.

Sequence Listing Free Text

SEQ ID NO: 1: AD' region sequence
SEQ ID NO: 2: ATP5b shRNA sequence
SEQ ID NO: 3: pAAV2/9 Vector sequence
SEQ ID NO: 4: U6-F primer
SEQ ID NO: 5: U6-R primer
SEQ ID NO: 6: HATP5b-F
SEQ ID NO: 7: hATP5b-R
SEQ ID NO: 8: A' region sequence
SEQ ID NO: 9: A region sequence
SEQ ID NO: 10: D' region sequence
SEQ ID NO: 11: D region sequence
SEQ ID NO: 12: Antisense sequence AO
SEQ ID NO: 13: Antisense sequence AO-c
SEQ ID NO: 14: Scrambled AD sequence
SEQ ID NO: 15: ITR primer-F
SEQ ID NO: 16: ITR primer-R
SEQ ID NO: 17: Antisense sequence AO4
SEQ ID NO: 18: Compliment AD sequence

The invention claimed is:

1. A method for producing an empty adeno-associated virus (AAV) particle encapsulating a nucleic acid, the method comprising:
   (1) preparing a linear nucleic acid fragment containing an AD sequence consisting of region A and region D' in an AAV inverted terminal repeat sequence (ITR) adjacent to each other, or a complementary sequence of the AD sequence, and a sequence of a gene of interest, wherein the AD sequence or the complementary sequence of the AD sequence does not anneal intramolecularly,
   (2) introducing the nucleic acid fragment prepared in step (1) into a cell that produces an empty AAV particle, and
   (3) culturing the cell obtained in step (2).

2. The method according to claim 1, wherein the nucleic acid fragment contains the AD sequence or the complementary sequence of the AD sequence, and the sequence of the gene of interest in order from the 5' end to the 3' end.

3. The method according to claim 1, wherein the nucleic acid fragment contains the sequence of the gene of interest, and the AD sequence or the complementary sequence of the AD sequence in order from the 5' end to the 3' end.

4. The method according to claim 1, wherein the step of preparing the nucleic acid fragment comprises amplification of the nucleic acid fragment by a nucleic acid amplification reaction.

5. The method according to claim 1, wherein the cell that produces an empty particle is a cell into which Cap gene and Rep gene of AAV, and helper function of AAV have been introduced.

6. The method according to claim 1, wherein the nucleic acid fragment is a double stranded nucleic acid or a single stranded nucleic acid.

7. The method according to claim 1, wherein a region for the AD sequence in the nucleic acid fragment is a double stranded nucleic acid, and a region for the sequence of the gene of interest in the nucleic acid fragment is a single stranded nucleic acid.

8. A linear nucleic acid fragment containing an AD sequence consisting of region A and region D' in an AAV inverted terminal repeat sequence (ITR) adjacent to each other, or a complementary sequence of the AD sequence, and a sequence of a gene of interest, wherein the AD sequence or the complementary sequence of the AD sequence does not anneal intramolecularly.

9. The nucleic acid fragment according to claim 8, which contains the AD sequence or the complementary sequence of the AD sequence, and the sequence of the gene of interest in order from the 5' end to the 3' end.

10. The nucleic acid fragment according to claim 8, which contains the sequence of the gene of interest, and the AD sequence or the complementary sequence of the AD sequence in order from the 5' end to the 3' end.

11. The nucleic acid fragment of claim 8, which is a double stranded nucleic acid or a single stranded nucleic acid.

12. The nucleic acid fragment according to claim 8, wherein a region for the AD sequence is a double stranded nucleic acid, and a region for the sequence of the gene of interest is a single stranded nucleic acid.

13. A nucleic acid-encapsulating empty AAV particle containing the linear nucleic acid fragment according to claim 8.

14. A nucleic acid-encapsulating empty AAV particle containing the linear nucleic acid fragment according to claim 9.

15. A nucleic acid-encapsulating empty AAV particle containing the linear nucleic acid fragment according to claim 10.

16. A nucleic acid-encapsulating empty AAV particle containing the linear nucleic acid fragment according to claim 11.

17. A nucleic acid-encapsulating empty AAV particle containing the linear nucleic acid fragment according to claim 12.

* * * * *

SEQUENCE LISTING

```
<160> NUMBER OF SEQ ID NOS: 18

<210> SEQ ID NO 1
<211> LENGTH: 61
<212> TYPE: DNA
<213> ORGANISM: Artificial Sequence
<220> FEATURE:
<223> OTHER INFORMATION: AD' region sequence

<400> SEQUENCE: 1
gcctcagtga gcgagcgagc gcgcagagag ggagtggcca actccatcac taggggttcc     60
```

-continued t                                                                          61

<210> SEQ ID NO 2
<211> LENGTH: 59
<212> TYPE: DNA
<213> ORGANISM: Artificial Sequence
<220> FEATURE:
<223> OTHER INFORMATION: ATP5b shRNA sequence

<400> SEQUENCE: 2
caccggctga ggctccagag ttcatggaaa cgaatttcca tgaactctgg agcctcagc         59

<210> SEQ ID NO 3
<211> LENGTH: 7389
<212> TYPE: DNA
<213> ORGANISM: Artificial Sequence
<220> FEATURE:
<223> OTHER INFORMATION: pAAV2/9 Vector

<400> SEQUENCE: 3
tcgaggacaa ccttagtgaa ggaattcgcg agtggtgggc tttgaaacct ggagcccctc         60
aacccaaggc aaatcaacaa catcaagaca acgctcgagg tcttgtgctt ccgggttaca        120
aataccttgg acccggcaac ggactcgaca aggggagcc ggtcaacgca gcagacgcgg         180
cggccctcga gcacgacaag gcctacgacc agcagctcaa ggccggagac aacccgtacc        240
tcaagtacaa ccacgccgac gccgagttcc aggagcggct caaagaagat acgtcttttg        300
ggggcaacct cgggcgagca gtcttccagg ccaaaaagag gcttcttgaa cctcttggtc        360
tggttgagga agcggctaag acggctcctg aaagaagag gcctgtagag cagtctcctc         420
aggaaccgga ctcctccgcg ggtattggca aatcgggtgc acagcccgct aaaaagagac        480
tcaatttcgg tcagactggc gacacagagt cagtcccaga ccctcaacca atcggagaac        540
ctcccgcagc cccctcaggt gtgggatctc ttacaatggc ttcaggtggt ggcgcaccag        600
tggcagacaa taacgaaggt gccgatggag tgggtagttc ctcgggaaat tggcattgcg        660
attcccaatg gctgggggac agagtcatca ccaccagcac ccgaacctgg gccctgccca        720
cctacaacaa tcacctctac aagcaaatct ccaacagcac atctggagga tcttcaaatg        780
acaacgccta cttcggctac agcacccccct gggggtattt tgacttcaac agattccact        840
gccacttctc accacgtgac tggcagcgac tcatcaacaa caactgggga ttccggccta        900
agcgactcaa cttcaagctc ttcaacattc aggtcaaaga ggttacggac aacaatggag        960
tcaagaccat cgccaataac cttaccagca cggtccaggt cttcacggac tcagactatc       1020
agctcccgta cgtgctcggg tcggctcacg agggctgcct cccgccgttc ccagcggacg       1080
ttttcatgat tcctcagtac gggtatctga cgcttaatga tggaagccag gccgtgggtc       1140
gttcgtcctt ttactgcctg gaatatttcc cgtcgcaaat gctaagaacg ggtaacaact       1200
tccagttcag ctacgagttt gagaacgtac ctttccatag cagctacgct cacagccaaa       1260
gcctggaccg actaatgaat ccactcatcg accaatactt gtactatctc tcaaagacta       1320
ttaacggttc tggacagaat caacaaacgc taaaattcag tgtggccgga cccagcaaca       1380
tggctgtcca gggaagaaac tacatacctg acccagcta ccgacaacaa cgtgtctcaa        1440
ccactgtgac tcaaaacaac aacagcgaat tgcttggcc tggagcttct tcttgggctc        1500
tcaatggacg taatagcttg atgaatcctg gacctgctat ggccagccac aaagaaggag       1560
aggaccgttt ctttcctttg tctggatctt taatttttgg caaacaagga actggaagag       1620

```
acaacgtgga tgcggacaaa gtcatgataa ccaacgaaga agaaattaaa actactaacc      1680
cggtagcaac ggagtcctat ggacaagtgg ccacaaacca ccagagtgcc caagcacagg      1740
cgcagaccgg ctgggttcaa aaccaaggaa tacttccggg tatggtttgg caggacagag      1800
atgtgtacct gcaaggaccc atttgggcca aaattcctca cacggacggc aactttcacc      1860
cttctccgct gatgggaggg tttggaatga agcacccgcc tcctcagatc ctcatcaaaa      1920
acacacctgt acctgcggat cctccaacgg ccttcaacaa ggacaagctg aactctttca      1980
tcacccagta ttctactggc caagtcagcg tggagatcga gtgggagctg cagaaggaaa      2040
acagcaagcg ctggaacccg gagatccagt acacttccaa ctattacaag tctaataatg      2100
ttgaatttgc tgttaatact gaaggtgtat atagtgaacc ccgcccatt ggcaccagat       2160 acctgactcg taatctgtaa ttgcttgtta atcaataaac cgtttaattc gtttcagttg      2220
aactttggtc tctgcgaagg gcgaattcgt ttaaacctgc aggactagag tcctgtatta      2280
gaggtcacgt gagtgttttg cgacattttg cgacaccatg tggtcacgct gggtatttaa      2340
gcccgagtga gcacgcaggg tctccatttt gaagcgggag gtttgaacgc gcagccgcca      2400
agccgaattc tgcagatatc catcacactg gcggccgctc gactagagcg gccgccaccg      2460
cggtggagct ccagcttttg ttccctttag tgagggttaa ttgcgcgctt ggcgtaatca      2520
tggtcatagc tgtttcctgt gtgaaattgt tatccgctca caattccaca caacatacga      2580
gccggaagca taaagtgtaa agcctggggg gcctaatgag tgagctaact cacattaatt      2640
gcgttgcgct cactgcccgc tttccagtcg ggaaacctgt cgtgccagct gcattaatga      2700
atcggccaac gcgcggggag aggcggtttg cgtattgggc gctcttccgc ttcctcgctc      2760
actgactcgc tgcgctcggt cgttcggctg cggcgagcgg tatcagctca ctcaaaggcg      2820
gtaatacggt tatccacaga atcaggggat aacgcaggaa agaacatgtg agcaaaaggc      2880
cagcaaaagg ccaggaaccg taaaaaggcc gcgttgctgg cgtttttcca taggctccgc      2940 cccccctgacg agcatcacaa aaatcgacgc tcaagtcaga ggtggcgaaa cccgacagga     3000
ctataaagat accaggcgtt tcccctggba agctccctcg tgcgctctcc tgttccgacc      3060
ctgccgctta ccggatacct gtccgccttt ctcccttcgg gaagcgtggc gctttctcat      3120
agctcacgct gtaggtatct cagttcggtg taggtcgttc gctccaagct gggctgtgtg      3180
cacgaacccc ccgttcagcc cgaccgctgc gccttatccg gtaactatcg tcttgagtcc      3240
aacccggtaa gacacgactt atcgccactg gcagcagcca ctggtaacag gattagcaga      3300
gcgaggtatg taggcggtgc tacagagttc ttgaagtggt ggcctaacta cggctacact      3360
agaaggacag tatttggtat ctgcgctctg ctgaagccag ttaccttcgg aaaaagagtt      3420
ggtagctctt gatccggcaa acaaaccacc gctggtagcg gtggtttttt tgtttgcaag      3480
cagcagatta cgcgcagaaa aaaaggatct caagaagatc ctttgatctt ttctacgggg      3540
tctgacgctc agtggaacga aaactcacgt taagggattt tggtcatgag attatcaaaa      3600
aggatcttca cctagatcct tttaaattaa aaatgaagtt ttaaatcaat ctaaagtata      3660
tatgagtaaa cttggtctga cagttaccaa tgcttaatca gtgaggcacc tatctcagcg      3720
atctgtctat ttcgttcatc catagttgcc tgactccccg tcgtgtagat aactacgata      3780
cgggagggct taccatctgg ccccagtgct gcaatgatac cgcgagaccc acgctcaccg      3840
gctccagatt tatcagcaat aaaccagcca gccggaaggg ccgagcgcag aagtggtcct      3900
gcaactttat ccgcctccat ccagtctatt aattgttgcc gggaagctag agtaagtagt      3960
tcgccagtta atagtttgcg caacgttgtt gccattgcta caggcatcgt ggtgtcacgc      4020
```

-continued

```
tcgtcgtttg gtatggcttc attcagctcc ggttcccaac gatcaaggcg agttacatga   4080
tcccccatgt tgtgcaaaaa agcggttagc tccttcggtc ctccgatcgt tgtcagaagt   4140
aagttggccg cagtgttatc actcatggtt atggcagcac tgcataattc tcttactgtc   4200
atgccatccg taagatgctt tctgtgactg gtgagtactc aaccaagtca ttctgagaat   4260
agtgtatgcg gcgaccgagt tgctcttgcc cggcgtcaat acgggataat accgcgccac   4320
atagcagaac tttaaaagtg ctcatcattg gaaaacgttc ttcggggcga aaactctcaa   4380
ggatcttacc gctgttgaga tccagttcga tgtaacccac tcgtgcaccc aactgatctt   4440
cagcatcttt tactttcacc agcgtttctg ggtgagcaaa aacaggaagg caaaatgccg   4500
caaaaaaggg aataagggcg acacggaaat gttgaatact catactcttc cttttttcaat   4560 attattgaag catttatcag ggttattgtc tcatgagcgg atacatattt gaatgtattt   4620
agaaaaataa acaaataggg gttccgcgca catttccccg aaaagtgcca cctaaattgt   4680
aagcgttaat attttgttaa aattcgcgtt aaattttgt taaatcagct catttttttaa   4740 ccaataggcc gaaatcggca aaatcccctta taaatcaaaa gaatagaccg agatagggtt   4800
gagtgttgtt ccagtttgga acaagagtcc actattaaag aacgtggact ccaacgtcaa   4860
agggcgaaaa accgtctatc agggcgatgg cccactacgt gaaccatcac cctaatcaag   4920
ttttttgggg tcgaggtgcc gtaaagcact aaatcggaac cctaaaggga gcccccgatt   4980
tagagcttga cggggaaagc cggcgaacgt ggcgagaaag gaagggaaga aagcgaaagg   5040
agcgggcgct agggcgctgg caagtgtagc ggtcacgctg cgcgtaacca ccacacccgc   5100
cgcgcttaat gcgccgctac agggcgcgtc ccattcgcca ttcaggctgc gcaactgttg   5160
ggaagggcga tcggtgcggg cctcttcgct attacgccag ctggcgaaag ggggatgtgc   5220
tgcaaggcga ttaagttggg taacgccagg gttttcccag tcacgacgtt gtaaaacgac   5280
ggccagtgag cgcgcgtaat acgactcact atagggcgaa ttgggtaccg gcccccccct   5340
cgatcgaggt cgacggtatc gggggagctc ggatccacta gtaacggccg ccagtgtgct   5400
ggattcggct ttatttaagc ccgagtgagc acgcagggtc tccattttga agcgggaggt   5460
ttgaacgcgc agccgccatg ccggggtttt acgagattgt gattaaggtc cccagcgacc   5520
ttgacgggca tctgcccggc atttctgaca gctttgtgaa ctgggtggcc gagaaggaat   5580
gggagttgcc gccagattct gacatggatc tgaatctgat tgagcaggca ccctgaccg   5640 tggccgagaa gctgcagcgc gactttctga cggaatggcg ccgtgtgagt aaggccccgg   5700
aggccctttt ctttgtgcaa tttgagaagg gagagagcta cttccacatg cacgtgctcg   5760
tggaaaccac cggggtgaaa tccatggttt gggacgtttt cctgagtcag attcgcgaaa   5820
aactgattca gagaatttac cgcgggatcg agccgacttt gccaaactgg ttcgcggtca   5880
caaagaccag aaatggcgcc ggaggcggga acaaggtggt ggatgagtgc tacatccccca   5940 attacttgct ccccaaaacc cagcctgagc tccagtgggc gtggactaat atggaacagt   6000
atttaagcgc ctgtttgaat ctcacggagc gtaaacggtt ggtggcgcag catctgacgc   6060
acgtgtcgca gacgcaggag cagaacaaag agaatcagaa tcccaattct gatgcgccgg   6120
tgatcagatc aaaaaacttca gccaggtaca tggagctggt cgggtggctc gtggacaagg   6180
ggattaccct ggagaagcag tggatccagg aggaccaggc ctcatacatc tccttcaatg   6240
cggcctccaa ctcgcggtcc caaatcaagg tgccttggac aatgcgggaa agattatgag   6300
cctgactaaa accgccccccg actacctggt gggccagcag cccgtggagg acatttccag   6360
```

-continued

```
caatcggatt tataaaattt tggaactaaa cgggtacgat ccccaatatg cggcttccgt        6420
ctttctggga tgggccacga aaaagttcgg caagaggaac accatctggc tgtttgggcc        6480
tgcaactacc gggaagacca acatcgcgga ggccatagcc cacactgtgc ccttctacgg        6540
gtgcgtaaac tggaccaatg agaactttcc cttcaacgac tgtgtcgaca agatggtgat        6600
ctggtgggag gaggggaaga tgaccgccaa ggtcgtggag tcggccaaag ccattctcgg        6660
aggaagcaag gtgcgcgtgg accagaaatg caagtcctcg gcccagatag acccgactcc        6720
cgtgatcgtc acctccaaca ccaacatgtg cgccgtgatt gacgggaact caacgacctt        6780
cgaacaccag cagccgttgc aagaccggat gttcaaattt gaactcaccc gccgtctgga        6840
tcatgacttt gggaaggtca ccaagcagga agtcaaagac tttttccggt gggcaaagga        6900
tcacgtggtt gaggtggagc atgaattcta cgtcaaaaag ggtggagcca agaaaagacc        6960
cgcccccagt gacgcagata taagtgagcc caaacgggtg cgcgagtcag ttgcgcagcc        7020
atcgacgtca gacgcggaag cttcgatcaa ctacgcggac aggtaccaaa acaaatgttc        7080
tcgtcacgtg ggcatgaatc tgatgctgtt tccctgcaga caatgcgaga gactgaatca        7140
gaattcaaat atctgcttca ctcacggtgt caaagactgt ttagagtgct ttcccgtgtc        7200
agaatctcaa cccgtttctg tcgtcaaaaa ggcgtatcag aaactgtgct acattcatca        7260
catcatggga aaggtgccag acgcttgcac tgcttgcgac ctggtcaatg tggacttgga        7320
tgactgtgtt tctgaacaat aaatgactta aaccaggtat ggctgccgat ggttatcttc        7380
cagattggc                                                              7389
```

```
<210> SEQ ID NO 4
<211> LENGTH: 20
<212> TYPE: DNA
<213> ORGANISM: Artificial Sequence
<220> FEATURE:
<223> OTHER INFORMATION: U6-F primer

<400> SEQUENCE: 4
ggactatcat atgcttaccg                                                    20

<210> SEQ ID NO 5
<211> LENGTH: 20
<212> TYPE: DNA
<213> ORGANISM: Artificial Sequence
<220> FEATURE:
<223> OTHER INFORMATION: U6-R primer

<400> SEQUENCE: 5
gtttcgtcct ttccacaaga                                                    20

<210> SEQ ID NO 6
<211> LENGTH: 22
<212> TYPE: DNA
<213> ORGANISM: Artificial Sequence
<220> FEATURE:
<223> OTHER INFORMATION: hATP5b-F primer

<400> SEQUENCE: 6
ggtcctgaga ctttgggcag aa                                                 22

<210> SEQ ID NO 7
<211> LENGTH: 20
<212> TYPE: DNA
<213> ORGANISM: Artificial Sequence
<220> FEATURE:
<223> OTHER INFORMATION: hATP5b-R primer
```

-continued

```
<400> SEQUENCE: 7
cctcagcatg aatgggagca                                              20

<210> SEQ ID NO 8
<211> LENGTH: 41
<212> TYPE: DNA
<213> ORGANISM: Artificial Sequence
<220> FEATURE:
<223> OTHER INFORMATION: A' region sequence

<400> SEQUENCE: 8
ttggccactc cctctctgcg cgctcgctcg ctcactgagg c                      41

<210> SEQ ID NO 9
<211> LENGTH: 41
<212> TYPE: DNA
<213> ORGANISM: Artificial Sequence
<220> FEATURE:
<223> OTHER INFORMATION: A region sequence

<400> SEQUENCE: 9
gcctcagtga gcgagcgagc gcgcagagag ggagtggcca a                      41

<210> SEQ ID NO 10
<211> LENGTH: 20
<212> TYPE: DNA
<213> ORGANISM: Artificial Sequence
<220> FEATURE:
<223> OTHER INFORMATION: D' region sequence

<400> SEQUENCE: 10
ctccatcact aggggttcct                                              20

<210> SEQ ID NO 11
<211> LENGTH: 20
<212> TYPE: DNA
<213> ORGANISM: Artificial Sequence
<220> FEATURE:
<223> OTHER INFORMATION: D region sequence

<400> SEQUENCE: 11
aggaacccct agtgatggag                                              20

<210> SEQ ID NO 12
<211> LENGTH: 15
<212> TYPE: DNA
<213> ORGANISM: Artificial
<220> FEATURE:
<223> OTHER INFORMATION: Antisense sequence AO
<220> FEATURE:
<221> NAME/KEY: modified_base
<222> LOCATION: (1)..(3)
<223> OTHER INFORMATION: LNA
<220> FEATURE:
<221> NAME/KEY: modified_base
<222> LOCATION: (1)/\(2)
<223> OTHER INFORMATION: Phosphorothioate linkage
<220> FEATURE:
<221> NAME/KEY: modified_base
<222> LOCATION: (2)/\(3)
<223> OTHER INFORMATION: Phosphorothioate linkage
<220> FEATURE:
<221> NAME/KEY: modified_base
<222> LOCATION: (3)/\(4)
<223> OTHER INFORMATION: Phosphorothioate linkage
<220> FEATURE:
<221> NAME/KEY: modified_base
<222> LOCATION: (4)/\(5)
```

```
<223> OTHER INFORMATION: Phosphorothioate linkage
<220> FEATURE:
<221> NAME/KEY: modified_base
<222> LOCATION: (5)/\(6)
<223> OTHER INFORMATION: Phosphorothioate linkage
<220> FEATURE:
<221> NAME/KEY: modified_base
<222> LOCATION: (6)/\(7)
<223> OTHER INFORMATION: Phosphorothioate linkage
<220> FEATURE:
<221> NAME/KEY: modified_base
<222> LOCATION: (7)/\(8)
<223> OTHER INFORMATION: Phosphorothioate linkage
<220> FEATURE:
<221> NAME/KEY: modified_base
<222> LOCATION: (8)/\(9)
<223> OTHER INFORMATION: Phosphorothioate linkage
<220> FEATURE:
<221> NAME/KEY: modified_base
<222> LOCATION: (9)/\(10)
<223> OTHER INFORMATION: Phosphorothioate linkage
<220> FEATURE:
<221> NAME/KEY: modified_base
<222> LOCATION: (10)/\(11)
<223> OTHER INFORMATION: Phosphorothioate linkage
<220> FEATURE:
<221> NAME/KEY: modified_base
<222> LOCATION: (11)/\(12)
<223> OTHER INFORMATION: Phosphorothioate linkage
<220> FEATURE:
<221> NAME/KEY: modified_base
<222> LOCATION: (12)/\(13)
<223> OTHER INFORMATION: Phosphorothioate linkage
<220> FEATURE:
<221> NAME/KEY: modified_base
<222> LOCATION: (13)/\(14)
<223> OTHER INFORMATION: Phosphorothioate linkage
<220> FEATURE:
<221> NAME/KEY: modified_base
<222> LOCATION: (13)..(14)
<223> OTHER INFORMATION: LNA
<220> FEATURE:
<221> NAME/KEY: modified_base
<222> LOCATION: (14)/\(15)
<223> OTHER INFORMATION: Phosphorothioate linkage

<400> SEQUENCE: 12
ttgatggcct gcttg                                                             15

<210> SEQ ID NO 13
<211> LENGTH: 16
<212> TYPE: DNA
<213> ORGANISM: Artificial
<220> FEATURE:
<223> OTHER INFORMATION: Antisense sequence AO-c
<220> FEATURE:
<221> NAME/KEY: modified_base
<222> LOCATION: (1)..(3)
<223> OTHER INFORMATION: LNA
<220> FEATURE:
<221> NAME/KEY: modified_base
<222> LOCATION: (1)/\(2)
<223> OTHER INFORMATION: Phosphorothioate linkage
<220> FEATURE:
<221> NAME/KEY: modified_base
<222> LOCATION: (2)/\(3)
<223> OTHER INFORMATION: Phosphorothioate linkage
<220> FEATURE:
<221> NAME/KEY: modified_base
<222> LOCATION: (3)/\(4)
<223> OTHER INFORMATION: Phosphorothioate linkage
<220> FEATURE:
<221> NAME/KEY: modified_base
<222> LOCATION: (4)/\(5)
<223> OTHER INFORMATION: Phosphorothioate linkage
<220> FEATURE:
<221> NAME/KEY: modified_base
```

<222> LOCATION: (5)∧(6)
<223> OTHER INFORMATION: Phosphorothioate linkage
<220> FEATURE:
<221> NAME/KEY: modified_base
<222> LOCATION: (6)∧(7)
<223> OTHER INFORMATION: Phosphorothioate linkage
<220> FEATURE:
<221> NAME/KEY: modified_base
<222> LOCATION: (7)∧(8)
<223> OTHER INFORMATION: Phosphorothioate linkage
<220> FEATURE:
<221> NAME/KEY: modified_base
<222> LOCATION: (8)∧(9)
<223> OTHER INFORMATION: Phosphorothioate linkage
<220> FEATURE:
<221> NAME/KEY: modified_base
<222> LOCATION: (9)∧(10)
<223> OTHER INFORMATION: Phosphorothioate linkage
<220> FEATURE:
<221> NAME/KEY: modified_base
<222> LOCATION: (10)∧(11)
<223> OTHER INFORMATION: Phosphorothioate linkage
<220> FEATURE:
<221> NAME/KEY: modified_base
<222> LOCATION: (11)∧(12)
<223> OTHER INFORMATION: Phosphorothioate linkage
<220> FEATURE:
<221> NAME/KEY: modified_base
<222> LOCATION: (12)∧(13)
<223> OTHER INFORMATION: Phosphorothioate linkage
<220> FEATURE:
<221> NAME/KEY: modified_base
<222> LOCATION: (14)..(16)
<223> OTHER INFORMATION: LNA
<220> FEATURE:
<221> NAME/KEY: modified_base
<222> LOCATION: (14)..(14)
<223> OTHER INFORMATION: m5c
<220> FEATURE:
<221> NAME/KEY: modified_base
<222> LOCATION: (14)∧(15)
<223> OTHER INFORMATION: Phosphorothioate linkage
<220> FEATURE:
<221> NAME/KEY: modified_base
<222> LOCATION: (15)∧(16)
<223> OTHER INFORMATION: Phosphorothioate linkage
<220> FEATURE:
<221> NAME/KEY: modified_base
<222> LOCATION: (16)..(16)
<223> OTHER INFORMATION: m5c

<400> SEQUENCE: 13
tagcttgtcc catctc                                          16

<210> SEQ ID NO 14
<211> LENGTH: 61
<212> TYPE: DNA
<213> ORGANISM: Artificial
<220> FEATURE:
<223> OTHER INFORMATION: Scrambled AD sequence

<400> SEQUENCE: 14
atggcggcac ggcgtgctag cgatcacagt gccagacgtg ctctgtgaga gcggcaacag    60
c                                                          61

<210> SEQ ID NO 15
<211> LENGTH: 21
<212> TYPE: DNA
<213> ORGANISM: Artificial
<220> FEATURE:
<223> OTHER INFORMATION: ITR primer-F

<400> SEQUENCE: 15

-continued

```
ggaaccccta gtgatggagt t                                                    21

<210> SEQ ID NO 16
<211> LENGTH: 21
<212> TYPE: DNA
<213> ORGANISM: Artificial
<220> FEATURE:
<223> OTHER INFORMATION: ITR primer-R

<400> SEQUENCE: 16
gcctcagtga gcgagcgagc g                                                    21

<210> SEQ ID NO 17
<211> LENGTH: 18
<212> TYPE: DNA
<213> ORGANISM: Artificial
<220> FEATURE:
<223> OTHER INFORMATION: Antisense sequence AO4

<400> SEQUENCE: 17
gccaaacctc ggcttacc                                                        18

<210> SEQ ID NO 18
<211> LENGTH: 61
<212> TYPE: DNA
<213> ORGANISM: Artificial
<220> FEATURE:
<223> OTHER INFORMATION: Compliment AD sequence

<400> SEQUENCE: 18
aggaacccct agtgatggag ttggccactc cctctctgcg cgctcgctcg ctcactgagg       60
c                                                                          61
```